United States Patent [19]

Olivieri et al.

[11] Patent Number: 4,666,840

[45] Date of Patent: May 19, 1987

[54] PROCESS FOR THE PREPARATION OF L-α-AMINOACIDS

[75] Inventors: Roberto Olivieri, Monterotondo; Giancarlo E. Bianchi, Rome; Eugenio Fascetti, Rome; Felice Centini, Rome, all of Italy

[73] Assignee: Sclavo S.p.A., Siena, Italy

[21] Appl. No.: 696,775

[22] Filed: Jan. 31, 1985

[30] Foreign Application Priority Data

Feb. 2, 1984 [IT] Italy ............................ 19403 A/84

[51] Int. Cl.$^4$ .................... C12N 9/78; C12P 13/04; C12P 41/00
[52] U.S. Cl. .................... 435/106; 435/227; 435/280
[58] Field of Search ............... 435/106, 170, 227, 280

[56] References Cited

U.S. PATENT DOCUMENTS

| | | | |
|---|---|---|---|
| 3,964,970 | 6/1976 | Dinelli et al. | 435/106 |
| 4,065,353 | 12/1977 | Cecere et al. | 435/129 |
| 4,094,741 | 6/1978 | Yamada et al. | 435/280 |
| 4,111,749 | 9/1978 | Degen et al. | 435/280 |
| 4,205,183 | 5/1980 | Hong | 435/280 |
| 4,237,227 | 12/1980 | Yamada et al. | 435/280 |
| 4,242,452 | 12/1980 | Yamada et al. | 435/280 |
| 4,248,967 | 2/1981 | Viglia et al. | 435/106 |
| 4,312,948 | 12/1982 | Olivieri et al. | 435/106 |

OTHER PUBLICATIONS

*Berichte* 384, "A. Mouneyrat: Verwandlung der αAminosäuren in Phenylhydantoine," pp. 2393-2396 (1900).

Wahru, Sun, "Screening of Strains Producing Dihydropyrimidinase and Fermentation Conditions", *Weishengwu Xuebao*, 1983, 23(3).

*Primary Examiner*—Thomas G. Wiseman
*Assistant Examiner*—Elizabeth C. Weimar
*Attorney, Agent, or Firm*—Hedman, Gibson, Costigan & Hoare

[57] ABSTRACT

The process of the invention is useful for the preparation of L-α-aminoacids and is based on the use of an N-carbamyl-α-aminoacid compound which is contacted with a E.C.3.5.2.2, a dihydropyrimidine hydrolase, enzyme to form a D-hydantoin. The D-hydantoin is hydrolyzed and racemized to form the D-N-carbamyl-α-aminoacid and the L-N-carbonyl-α-aminoacid. The L-N-carbamyl-α-aminoacid is thereafter transformed into the corresponding L-α-aminoacid.

14 Claims, No Drawings

PROCESS FOR THE PREPARATION OF L-α-AMINOACIDS

The present invention relates to a process for the preparation of L-α-aminoacids with formula

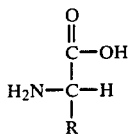     (I)

wherein R is an aromatic, substituted aromatic, aliphatic or substituted aliphatic group.

In particular, the present invention relates to an enzymatic process for preparing L-α-aminoacids of formula (I), wherein R is a group selected from

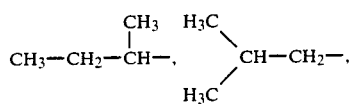

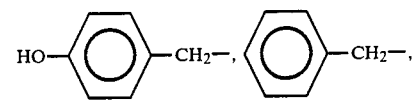

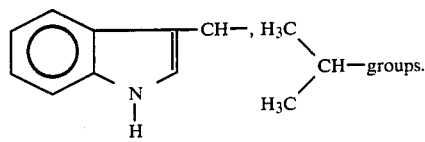

Compounds of formula (I) are useful as intermediates for the preparation of compounds used in pharmaceutical and chemical industry.

As an example, L-α-phenylalanine is a highly valuable product, in that it can be used in the synthesis of Aspartame, useful as sweetening agent.

Compounds of formula (I) are obtained, by means of a known process, by means of the hydrolysis of proteins and of the isolation of aminoacids from the reaction mixture.

This process is however expensive due to the use of valuable starting materials, to the number of required treatments, and due to the overall poor yields.

According to the published Japanese Patent Appl. No. 13850/1967, L-α-aminoacids are prepared from hydantoins with an unsymmetrical carbon atom (5-substituted hydantoins) by means of a fermentation process in the presence of an enzyme.

The reaction product is separated and recovered from the reaction mixture.

It has been now found, and is the purpose of the present invention, a simple and cheap process for the preparation of L-α-aminoacids.

According to the present invention, L-α-aminoacids

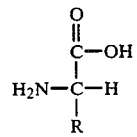     (I)

wherein R is an aromatic, substituted aromatic, aliphatic or substituted aliphatic groups are accordingly prepared, by means of a process characterized in that:

(a) the N-carbamyl-α-aminoacid compound

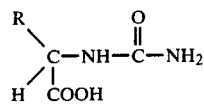     (II)

wherein R has the above-indicated meaning, in the form of D-N-carbamyl-α-aminoacid and L-N-carbamyl-α-aminoacid is contacted, in a liquid reaction mixture, at a pH of from 6.0 to 7.0 and at a temperature of from 20° C. to 40° C., with an enzyme to give a compound

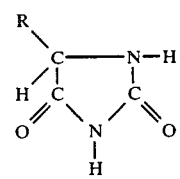     (III)

wherein R has the above-reported meaning in the form of D-hydantoin and a compound

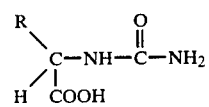     (IV)

wherein R has the above-reported meaning, in the form of L-N-carbamyl-α-aminoacid;

(b) D-hydantoin is separated from the reaction mixture and is hydrolyzed and racemized to D-N-carbamyl-α-aminoacid and L-N-carbamyl-α-aminoacid;

(c) L-N-carbamyl-α-aminoacid is transformed into the corresponding L-α-aminoacid;

(d) L-α-aminoacid is separated and recovered from said reaction mixture.

According to the process of the present invention, in step (a) a compound of formula

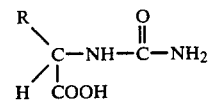     (II)

wherein R is a group selected from

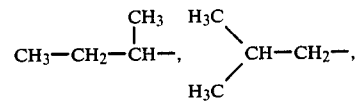

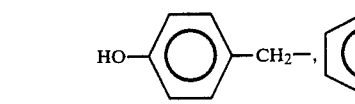

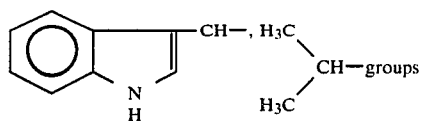

in the form of D-N-carbamyl-α-aminoacid and of L-N-carbamyl-α-aminoacid is submitted to an enzymatic reaction, in a liquid reaction mixture, at a pH of from 6.0 to 7.0, and at a temperature of from 20° C. to 40° C., to give a compound

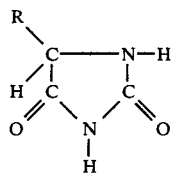
(III)

wherein R has the above-indicated meaning, in the form of D-hydantoin, and a compound

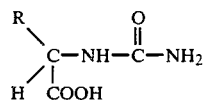
(IV)

wherein R has the above-indicated meaning, in the form of L-N-carbamyl-α-aminoacid.

The enzyme used to the purpose is a dihydropyrimidine hydrolase E.C. 3.5.2.2 known in the art because of its capability of selectively hydrolyzing the hydantoins with an unsymmetrical carbon atom to D-N-carbamyl-α-aminoacids.

The enzyme can be obtained from extracts of animal organs or from microorganisms pertaining to the genus Pseudomonas, Achromobacter, Corynebacterium, Brevibacterium, Microbacterium, Artrobacter, Agrobacterium, Acrobacter, Klebsiella, Sarcina, Protaminobacter, Streptomyces, Actinomyces, Candida, Rhodotorula, Pichia or Paecilomyces.

In the preferred embodiment of the invention, the enzyme has been extracted from calf liver, according to the method described by D. P. Wallach and S. Grisolia in J. of Biol. Chem. 226, 277 (1957) and from the following microorganisms:

| Agrobacterium radiobacter | NRRL B | 11291 |
|---|---|---|
| Bacillus brevis | NRRL B | 11080 |
| Bacillus stearothermophilms | NRRL B | 11079 |
| Pseudomonas sp | CBS | 14575 |
| Pseudomonas sp | CBS | 14675 |
| Pseudomonas sp | ATCC | 11299 |
| Pseudomonas fluorescens | ATCC | 11250 |
| Pseudomonas putida | ATCC | 12633 |
| Pseudomonas desmolytica | NCIB | 8859 |

The taxonomic characteristics of above-indicated microorganisms have been studied by using methods described by M. J. Pelczav in "Manual of Microbiological Methods" and the identification has been carried out according to "Bergey's Manual of Determinative Bacteriology" VIII Ed., 1974.

The above-indicated microorganisms are cultured under aerobic conditions, in a liquid culture medium containing sources of nitrogen, of carbon, of phosphorus and mineral salts.

Sources of carbon suitable to this purpose are carbohydrates such as: glucose, saccharose, organic acids, alcohols and hydrocarbons.

Nitrogen sources which may be used in culture medium comprise: organic and inorganic ammonium salts, such as ammonium sulphate, ammonium chloride, ammonium nitrate, urea and ammonia.

Inorganic salts which may be used in the present invention comprise: potassium phosphate, sodium phosphate, magnesium sulphate, calcium carbonate, ferrous sulphate, manganese sulphate and zinc sulphate.

The culture medium, having the above-indicated composition, is maintained at a pH of from 5.5 to 9.0 and at a temperature of from 20° C. to 40° C.

Typically, the culture is carried out at a neutral pH, at a temperature of 30° C., and over a 24-hour time period.

Under the preferred growth conditions, the microorganisms produce, inside their cells, an enzyme capable of transforming compound (II) into compound (III) and into compound (IV).

The microbial cells are generally removed from the culture medium, by means of processes known in the art, such as by filtration or centrifugation, and are subsequently brought into contact with compound (II) in a liquid reaction mixture.

Alternatively, the microbial cells, after having been separated from the culture medium, are treated with rotary disintegrators, French-pressure, ultra-sounds, and the proteinic fraction, separated by conventional methods, is used in the enzymatic reaction of compound (II).

A further technical and financial improvement of the present invention is achieved by immobilizing the enzyme or the microorganisms containing it within fibrous structures as disclosed in Italian Pat. No. 836.462.

The quantity of microbial cells used in the enzymatic reaction of compound (II) is generally such as to have a cells/compound (II) weight ratio of from 1/40 to 1/100. The enzymatic reaction is preferably carried out at a temperature of 30° C., at a pH of 6.5 and over a time of 24 hours.

By operating under said conditions, the compound (III) is obtained as a solid, and the compound (IV) is obtained in solution.

The temperature of the so-obtained dispersion is adjusted within the range of from 0° to 10° C., and the pH of said dispersion is adjusted within the range of from 4.0 to 5.5 until a complete or substantially complete precipitating of compound (III) is obtained.

In the step (b) of the present invention, any known techniques are used for the separation and the hydrolysis of compound (III).

Compound (III) is generally separated by filtering, centrifuging, or by another suitable technique, and the hydrolysis of said compound is carried out in the liquid phase, in the presence of 1N sodium hydroxide, at a temperature of 90° C., and for a time of about 10 hours.

At the end of the reaction, a compound of formula (II) is obtained, which is subsequently recycled to the step (a).

In step (c), the transformation of L-N-carbamyl-α-aminoacid (IV) into L-α-aminoacid (I) is carried out according to known methods.

The compound (IV) present in the solution, after the withdrawal of D-hydantoin, is brought into contact with nitrous acid, with a molar ratio of compound (IV)

to nitrous acid of from 1/1 to 1/5; at a temperature of 30° C., and for a time of from 4 to 5 hours.

Alternatively, the transformation in step (c) may be carried out after a preliminary precipitation and separation of compound (IV) from the filtered solution obtained in step (b).

Compound (IV) is precipitated, after having removed the microbial cells, by adjusting the temperature at a value of 10° C., and the pH at a value of 3.1, and is separated by processes well known in the art.

In any case, at the end of this transformation reaction, the separation and recovery of formed L-α-aminoacid is carried out in step (d) by using an ion-exchange resin.

In a preferred embodiment of the invention, the reaction of transformation of L-N-carbamyl-α-aminoacid into the corresponding L-α-aminoacid, and the separation of L-α-aminoacid (I) are carried out as a single step.

A mixture consisting of L-N-carbamyl-α-aminoacid (IV) and sodium nitrite is fed to a chromatographic column loaded with an acidic ion-exchange resin, and the solution is circulated for a time of 4–5 hours. The compound L-α-aminoacid (I) formed during the reaction is fixed by the acidic groups present on the resin.

L-α-aminoacid is then recovered by elution with a 2N aqueous solution of ammonium hydroxide. The eluted solution is concentrated to dryness, is neutralized and an optically pure L-α-aminoacid is obtained.

The following experimental Examples are illustrative and not limitative of the invention.

EXAMPLE 1

A culture broth is prepared, having the following composition:

| | |
|---|---|
| meat peptone | 5 g |
| meat extract | 3 g |
| glucose | 5 g |
| water | 1 l |
| pH | 7.2 |

100 ml of said culture broth are distributed inside conical Erlenmeyer flasks of 0.5 l capacity, and sterilized at 110° C. for 30 minutes.

The conical flasks are inoculated with an amount corresponding to that collected by a Pt-wire fork, of a culture of Pseudomonas CBS 14575 stock, previously cultured at 30° C. over 24 hours on slants of a culture medium having the above-indicated composition, and solidified with 20 g/l of agar (DIFCO).

The thus-inoculated conical flasks are maintained at a temperature of 30° C., under orbital shaking (220 rpm) for 24 hours.

At the end of said time period, 1 ml of culture broth is drawn, under sterile conditions, and is transferred into a conical Erlenmeyer flask of 0.5 l capacity, containing 100 ml of culture medium having the above-reported composition.

The conical flasks are kept at a temperature of 30° C. for a time of 24 hours.

At the end of said time period, microbial cells are separated from the reaction medium by centrifugation, and are washed with an equal volume of physiological solution (8 g of NaCl, 1 l of water).

After centrifugation, 200 mg of microbial cells are suspended in a solution of 8 g of DL-N-carbamyl-phenylalanine (compound (II) with

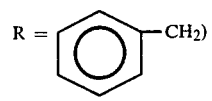

in 50 ml of water with a pH of 6.5.

The suspension is kept stirred at a temperature of 30° C. for 24 hours.

At the end of said time period, a dispersion is obtained, which is conditioned at a temperature of 10° C. and at a pH of 5.5, until a complete precipitation of product (III) is obtained.

The precipitated compound is then filtered and washed with water. An amount of 3,6 D-benzylhydantoin is thus obtained, whose identity is confirmed by I.R., N.M.R. and elemental analysis.

D-Benzylhydantoin is hydrolized and racemized to D-N-carbamyl phenylalanine and L-N-carbamyl-phenylalanine, by treatment with 40 ml of a 1N aqueous solution of NaOH at a temperature of 90° C. for 10 hours.

The racemic mixture so obtained is recycled.

L-N-carbamylphenylalanine present in solution, after that D-benzylhydantoin has been removed, is precipitated, the microbial cellular mass being preliminarly separated by centrifuging, at a temperature of 10° C. and at a pH of 3.1.

The so-obtained precipitate is separated by filtration, and dried in vacuo.

An amount of 3.8 g of L-N-carbamylphenylalanine is so obtained, whose identity is confirmed by I.R., N.M.R. and elemental analyses, with a rotatory optical power $[\alpha]_D^{25°\ C.} = 38.5$ (C=1%, 1N NH3). To a suspension of 3.8 g (18.3 mole) of L-N-carbamylphenylalanine in 100 ml of water, 1.6 g (23.8 mmole) of NaNO2 are added. The suspension is subsequently made soluble by means of the addition of 1N ammonia water.

The solution is fed into a chromatographic column (20 mm in diameter, 30 mm in length) loaded with 30 g of an ion-exchange resin, Amberlite IR 120, and recycled for 4 hours. L-α-phenylalanine being formed during the reaction between L-N-carbamylphenylalanine and nitrous acid is adsorbed on the resin.

At the end of the reaction, the column is washed with water and L-α-phenylalanine is eluted with a 2N aqueous solution of ammonium hydroxide.

Eluted solution is concentrated to dryness. An amount of 2.73 g (16.5 mmole) of L-α-phenylalanine with an optical power $[\alpha]_D^{20°} = -34.3$ (C=1.94 in water) is so obtained.

EXAMPLE 2

The process is carried out as in Example 1, using as starting material an amount of 5 g of DL-N-carbamyl-valine (compound (II) wherein

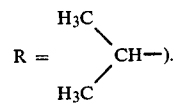

The enzymatic reaction is carried out at a temperature of 30° C. for 24 hours and, after cooling of the dispersion to a temperature of 10° C., and adjustment of its pH to 5.5, 2.3 g of D-isopropylhydantoin are separated.

L-N-carbamylvaline is then transformed, and the corresponding aminoacid is separated. An amount of 1.42 g of L-α-valine with rotatory optical power $[\alpha]_D^{20°} = +23.8$ (C=5%, 1N HCl) is thus obtained, by operating as described in Example 1.

EXAMPLE 3

The process is carried out as described in Example 1, using as the substrate an amount of 9 g of DL-N-carbamylleucine (compound (II)) with

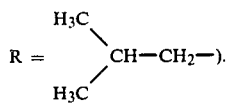

At the end of the enzymatic reaction, 4.2 g of D-2-methylpropylhydantoin, whose identity is confirmed by I.R., NMR, and elemental analysis are obtained.

L-N-Carbamylleucine is then converted, and the corresponding aminoacid is separated.

An amount of 2,75 g of L-α-leucine with a rotatory optical power $[\alpha]_D^{20°} = +12.0$ (C=2.5, 1N HCl) is obtained, by operating as described in Example 1.

EXAMPLE 4

The process is carried out as in Example 1, using as the enzymatic catalyst, 2 g of acetone powder of calf liver, obtained as described by D. P. Wallach and S. Grisolia in J. of Biol. Chem. 226, 277 (1957).

The enzymatic reaction is carried out at a temperature of 30° C. and for a time of 24 hours.

After cooling of the dispersion to a temperature of 10° C., and correction of pH to a value of 5.5, 3.2 g of D-benzylhydantoin are separated.

L-N-carbamyl-phenylalanine is then transformed into the corresponding aminoacid, and 2,68 g of L-α-phenylalanine with a rotatory optical power $[\alpha]_D^{20°} = -34.1$ (C=1.94, in water) are obtained, by operating as described in Example 1.

We claim:

1. Process for the preparation of L-α-aminoacids

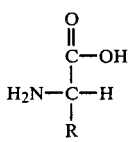 (I)

wherein R is an aromatic, substituted aromatic, aliphatic or substitued aliphatic group said process comprising:

(a) contacting an N-carbamyl-α-aminoacid compound of the formula:

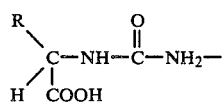 (II)

wherein R has the above-indicated meaning, and in the form of D-N-carbamyl-α-aminoacid and L-N-carbamyl-α-aminoacid in a liquid reaction mixture at a pH of from 6.0 to 7.0 and at a temperature of from 20° C. to 40° C., with a dihydropyrimidine hydrolase E.C.3.5.2.2 enyzme to give a compound of the formula:

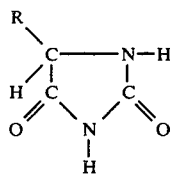 (III)

wherein R has the above-indicated meaning, in the form of D-hydantoin, and a compound of the formula:

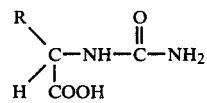

wherein R has the above-indicated meaning, as an L-N-carbamyl-α-aminoacid;

(b) separating the D-hydantoin from the reaction mixture and hydrolyzing and racemizing said D hydantoin to the D-N-carbamyl-α-aminoacid and the L-N-carbamyl-α-aminoacid;

(c) transforming the L-N-carbamyl-α-aminoacid into the corresponding L-α-aminoacid; and (d) separating the L-α-aminoacid from the reaction mixture.

2. Process as claimed in claim 1, wherein R in compounds (I), (II) and (III) is selected from the group consisting of

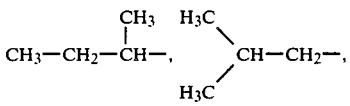

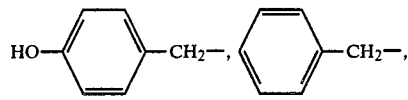

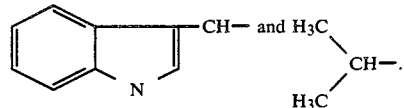

3. Process as claimed in claim 1, wherein the enzyme is obtained from calf liver.

4. Process as claimed in claim 1, wherein the enzyme is produced by a microorganism.

5. Process as claimed in claim 4, wherein the microorganism is a member of the genus Pseudomonas.

6. Process as claimed in claim 5, wherein the microorganism is selected from the group consisting of Pseudomonas CBS 14575, Pseudomonas CBS 14675, Pseudomonas ATCC 11299, Pseudomonas desmolytica NCIB 8859, Pseudomonas fluorescens ATCC 11250 and Pseudomonas putida ATCC 12633.

7. Process as claimed in claim 4, wherein the microorganism is a member of the genus Bacillus.

8. Process as claimed in claim 7, wherein the microorganism is selected from the group consisting of Bacillus brevis NRRL B 11080 and Bacillus stearothermophilms NRRL B 11079.

9. Process as claimed in claim 4, wherein the microorganism is a member of the genus Agrobacterium.

10. Process as claimed in claim 9, wherein the microorganism is Agrobacterium radiobacter NRRL B 11291.

11. Process as claimed in claim 1, wherein step (a) is carried out at the temperature of 30° C. and at a pH of 6.5.

12. Process as claimed in claim 1, wherein the hydrolysis reaction in step (b) is carried out in the liquid phase in the presence of 1N NaOH, at a temperature of 90° C. and for a time period of 10 hours.

13. Process as claimed in claim 1, wherein the transformation in step (c) is carried out by means of nitrous acid at a temperature of 30° C. and for a time period of 4 hours.

14. Process as claimed in claim 1, wherein the separation in step (d) is carried out by means of a treatment with an ion-exchange resin.

* * * * *